United States Patent [19]

Di Giacomo et al.

[11] 4,330,153

[45] May 18, 1982

[54] IDENTIFICATION OF FLUID FLOW UNDER IN-SITU MINING CONDITIONS

[75] Inventors: Peter M. Di Giacomo, Mission Viejo; Won C. Park, Irvine, both of Calif.

[73] Assignee: Occidental Research Corporation, Irvine, Calif.

[21] Appl. No.: 182,522

[22] Filed: Aug. 29, 1980

[51] Int. Cl.$^3$ .................... E21B 43/28; E21C 41/14; G01N 31/22; G01N 33/24
[52] U.S. Cl. .................................... 299/1; 299/4; 299/5
[58] Field of Search ...................... 299/1, 4, 5; 175/41, 175/42, 46; 73/155, 151; 23/230 A

[56] References Cited

U.S. PATENT DOCUMENTS

| | | | |
|---|---|---|---|
| 2,868,625 | 1/1959 | Frank | 166/252 X |
| 2,935,612 | 5/1960 | Essington | 175/41 X |
| 3,205,353 | 9/1965 | Bray | 175/41 |
| 3,508,613 | 4/1970 | Huff et al. | 299/5 X |
| 3,508,876 | 4/1970 | Polly | 166/252 X |
| 3,890,007 | 6/1975 | Heinen et al. | 299/4 |
| 3,910,636 | 10/1975 | Hard | 299/5 |
| 3,912,330 | 10/1975 | Carnahan et al. | 299/4 |
| 4,079,783 | 3/1978 | Snavely et al. | 166/252 |

Primary Examiner—Stephen J. Novosad
Attorney, Agent, or Firm—Robert J. Baran

[57] ABSTRACT

The instant disclosure relates to a method of tracing the flow of a solution for extracting values from an ore, wherein such extraction leaves behind an extracted ore, which method comprises
(a) providing a material in said solution which will interact with said extracted ore to form a product, and
(b) detecting said product.

The instant invention is especially useful for the extraction of copper values from copper oxide ores such as chrysocolla, neotocite, malacite and cuprite. Preferably, the extraction solution is an acidic solution comprising sulfuric acid and said material is a fluorescent surface-active dye which forms an adsorption product with the porous gel-like aluminosilicate network which remains after extracting the copper values from the above ores. A sample of said extracted ore is obtained by drilling and such sample is irradiated with ultra-violet light, e.g. at a wavelength of from about 220 to about 400 nm, depending on the particular dye to detect such adsorption product. Preferably the fluorescent dye is selected from the group consisting of aniline and pyridine derivatives. More preferably, the surface-active fluorescent dye is a coumarin, e.g. 7-diethylamino-4-methyl coumarin.

27 Claims, No Drawings

IDENTIFICATION OF FLUID FLOW UNDER IN-SITU MINING CONDITIONS

BACKGROUND OF THE PRIOR ART

It is often desired to ascertain the flow pattern of water through porous underground formations such as ore bodies from which metals are extracted by solution mining processes. Methods for tracing the flow of water are many and varied, e.g. U.S. Pat. No. 2,868,625 teaches a method for tracing the flow of water by the incorporation of a small amount of a compound such as ethylenediaminetetraacetic acid into injection water and testing the water removed from a product well located at a point distant from the point of injection for such compound. This method makes it possible to follow the arrival of the injection water at several production wells from the injection well. However, the path of such water will not be detectable merely by analyzing the water at the production well. This method will only determine that the water is moved in some pathway from said injection well to the production well.

In U.S. Pat. No. 3,508,875 a different tracer is added to three different injection wells and the outflow from the production well is analyzed to determine the presence of each individual tracer. This method again allows the operator to determine whether the water is moving between any or all injection wells and the production well, however the exact flow path of the water is not known.

Other methods for tracing the flow of underground water include providing fluorescent dyes in water soluble form in said water and measuring the fluorescence of the outflow well.

None of these methods solve one of the basic problems found in 'in situ' solution mining processes. As used throughout this specification, the term 'in situ' solution mining refers to a process wherein an extraction solution is injected into the ground through one or more injection wells to contact a subterranean deposit of an ore, and a solution containing metal values dissolved from said ore is recovered from one or more production wells. In 'in situ' solution mining processes it is desirable to know whether the solution has been in contact with all of the ore. 'In situ' solution mining processes are disclosed generally in U.S. Pat. Nos. 3,910,636; 3,647,261; 3,574,599; 3,215,471; and 3,853,353. None of these patents discuss methods for insuring that all of the ore is contacted with the extraction solution. It is, however, known in the art that when extracting copper from feldspar ores, wherein an oxidizing agent is added to the sulfuric acid extraction solution, that the residue of the extracted feldspar contains ferric hydroxide. Samples may be taken by coring into the ore to determine whether ferric hydroxide is present. In locations where ferric hydroxide is found it is presumed that the leaching solution has been in contact with the ore. This method, however, does not rely on providing a material that will react with the extracted ore nor is this method suitable for ores containing low amounts of iron in association with the copper, e.g. oxide type ores chrysocolla. It is thus an object of the invention to provide a method for determining whether such copper oxide-type ores have been in contact with the copper extraction solution. Other objects of the instant invention will be obvious from the below specification.

SUMMARY OF THE INVENTION

The instant invention relates to a method of tracing the flow of a solution for extracting values from an ore, wherein such extraction leaves behind an extracted ore which method comprises (a) providing a material in said solution which will interact with said extracted ore to form a product, and (b) detecting said product.

The instant method is especially suitable for extracting copper from copper oxide-type ores such as chrysocolla, malachite, and cuprite.

In a preferred embodiment of the invention an aqueous acid solution is used to extract copper from said oxide-type ores. Said solution preferably will comprise a fluorescent surface-active dye as the material which interacts with said extracted ore to form a detectable product. As will be further explained below, this dye may be selected from the group consisting of pyridine and aniline derivatives a specific example of which is 7-diethylamino-4-methyl coumarin (DMC). This particular dye (DMC) is especially suitable for use with copper oxide containing ores since upon extraction with an acidic aqueous solution a porous gel-like network of aluminosilicate is left behind. The above pyridine and aniline derivatives expecially DMC will adsorb on such aluminosilicate to form a stable adsorption product.

Flouorescent materials which are useful in the method of the instant invention include compounds represented by the following general formulae:

COUMARIN DERIVATIVES

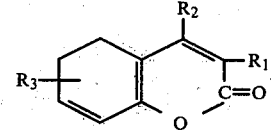

DISTRYLBIPHENYL DERIVATIVES

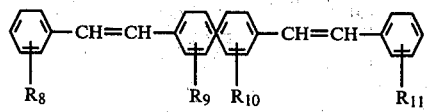

DIAMINOSTILBENEDISULFONIC ACID-CYANURIC CHLORIDE DERIVATIVES

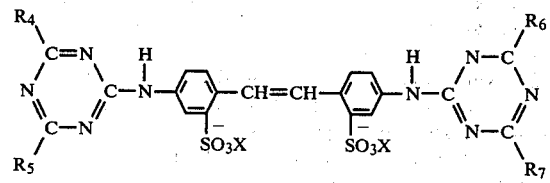

NAPHTHOTRIAZOLYSTILBENE DERIVATIVES

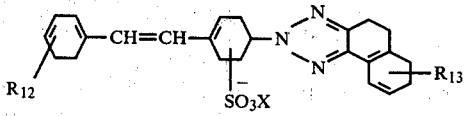

and
PYRAZOLINE DERIVATIVES

-continued

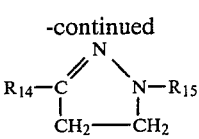

wherein said R groups may be selected from the group consisting of hydrogen, hydrocarbyl, and substituted hydrocarbyls, e.g. hydrocarbyl substituted with heteroatoms such as oxygen, nitrogen, halide, phosphorous and sulfur and X is selected from the group consisting of hydrogen, alkaline metal ions and alkaline earth metal ions. In general, the R groups may be selected to provide adsorption capacity to the fluorescent moiety represented by the general formula. For example, the R groups may represent amino groups such as alkylamino groups and hydroxylalkylamino groups (dimethylamino, diethylamino, 2-hydroxyethylamino, etc), sulfonic acid and sulfonate groups, morphilino groups, anilino groups, pyridinyl groups, sulfonamido groups, carboxylic acid and carboxylate groups, etc. For example, specific commercially available fluorescent dyes within the above formula include compound wherein:

$R_1$=hydrogen; $R_2$=methyl; and $R_3$=dimethylamino: 7-dimethylamino-4-methyl coumarin $R_1$=hydrogen; $R_2$=methyl; and $R_3$=diethylamino: 7-diethylamino-4-methyl coumarin $R_4$, $R_5$, $R_6$ and $R_7$=anilino: 4,4'-Bis[(4,6-dianilino-S-triazin-2-yl)amino]-2,2'-stilbenedisulfonic Acid and its disodium salt $R_4$ and $R_6$=anilino; $R_5$ and $R_7$=di(2-hydroxyethyl)amino: 4,4'-Bis[(4-anilino-6[Bis(2-hydroxyethyl)aminol]-s-triazin-2-yl)aminol]-2,2'-stilbenedisulfonic Acid and its disodium salt $R_4$ and $R_6$=anilino; $R_5$ and $R_7$=morpholino: 4,4'-Bis[(4-anilino-6-morpholino-s-triazin-2-yl)aminol]-2,2'-stilbenedisulfonic Acid and its disodium salt $R_4$ and $R_6$=anilino; $R_5$ and $R_7$=N-2-hydroxyethyl-N-methylamino:
4,4'-Bis[(4-anilino-6[N-2-hydroxyethyl-N-methylamino]-s-triazin-2-yl)amino]-2,2'-stilbenedisulfonic acid and its disodium salt.

$R_4$ and $R_6$=anilino; $R_5$ and $R_7$=(2-hydroxypropyl)amino: 4,4'-Bis[[4-anilino-6-[(2-hydroxylpropyl)amino]-s-triazin-2-yl]amino]-2,2'-stilbenedisulfonic acid and its disodium salt.

$R_8$ and $R_{11}$ are sulfonic acid or neutralized sulfonic acid groups and $R_9$ and $R_{10}$ are hydrogen;

(2,2[4,4'-Biphenylene divinylene]dibenzenesulfonic acid and the salts thereof such as the disodium salt and the dipotassium salt)

$R_{12}$ and $R_{13}$=hydrogen;
4-(2H-Naphthol[1,2-d]triazol-2yl)-2-stilbenesulfonic acid and the sodium or potassium salt thereof;

$R_{14}$=p-chlorphenyl; $R_{15}$ is p-sulfonamido phenyl p-[3-(p-chlorophenyl)-2-pyrazolin-1-yl]benzenesulfonicamide The fluorescent materials must also be easily detectable. The materials described above are easily detected by irradiating a sample of the extracted ore which contains said adsorbed materials at the appropriate U.V. wavelength, for example wavelengths of from 220 to 400 nm may be used. As further described below the sampling for the detectable product is preferably done by drilling into said extracted ore to obtain a core. The commercial drilling muds used in drilling are of a highly basic nature, therefore it is important that the dyes are not extracted under basic conditions otherwise they will not be recovered with the extracted ore. Fluorescent surface-active dyes which are deprotonated below a pH of 10 are preferred to thus insure the insolubility of the dye in the drilling mud. It has been found that pyridine and aniline derivatives of the above fluorescent materials are insoluble in high pH solutions and therefore extremely suitable for use in the method of the instant invention.

The above fluorescent materials are also favored since they strongly adsorb on the porous gel-like structure remaining after the extraction of copper from oxide type copper ores with acidic extraction solutions. Moreover, these fluorescent materials are soluble and stable in the acidic extraction solutions for long periods of time. Finally, these fluorescent materials are detectable at very low levels and therefore their use is economical in a commercial process.

DETAILED DESCRIPTION OF THE INVENTION

The specification below describes the preferred embodiment of the instant invention, i.e. the extraction of copper values from an oxide ore. However, the instant novel method is applicable to the extraction of other values from any ore in which such values are found.

The most suitable fluorescent material may be selected by reference to the chemical and physical nature of the ore remaining after the metal values have been extracted. For example, carboxylate derivatives of the above described fluorescent materials are suitable wherein the ore will include cationic moieties such as calcium after extraction. The amino and hydroxyamino derivatives are suitable where the ore will include anionic moieties such as aluminates or silicates after extraction.

1. Extraction Solution

Copper containing ores are easily extracted to obtain the metal values by means of acidic extraction solutions. Suitable extraction solutions are described in the U.S. Pat. Nos. 3,910,636; 3,853,636; 3,853,353; and 3,574,599 which are herein incorporated by reference for the disclosure of suitable extraction solutions. In general, the extraction solution for copper is an aqueous solution containing sulfuric acid at a level of from about 1 to about 100 grams, preferred from about 1 to about 50 grams of sulfuric acid per liter of solution. The solution will generally have a pH value of from about 0.2 to about 2.0 and more preferably between 0.5 to 1.5. Additives such as nitrates, oxidizing agents which are useful in extracting copper from feldspar type ores, etc. are not necessary in the extraction of the oxide ores which are especially suitable for treatment by the method of the instant invention.

2. The Material

The purpose of the material which is added to the extraction solution is to provide in such solution a compound which will react with the residue of extraction, i.e. the extracted ore, to leave behind a detectable product. Thus, one skilled in the art knowing which residue would be involved in the particular ore of interest would be able to select a material which would react therewith in a manner to enable detection by either physical or chemical means. Preferably, this material will be a surface-active dye which may adsorb on the surface of the residue to yield a product which can be detected by eye or by radiation outside the visible range of light. The material, of course, must be stable in the extraction solution in a form which will adsorb on the residue. It should be noted that it is possible to carry out the instant inventive process sequentially, i.e. by flowing first an extraction solution without said material to remove copper from the ore followed by a solution containing such material. However, it will be preferred for simplicity and economic reasons to provide a solution wherein the material is combined with the extraction solution.

The material must be stable during the recovery of the sample for analysis of the detectable product. In general, the sample will be recovered by drilling into the extracted ore deposit and recovering a core. The commercially useful drilling muds are generally basic in nature therefore it is desirable to utilize a material which will form a detectable product that is stable to basic drilling compounds.

The preferred materials useful for forming detectable products with said extracted ore are the surface-active fluorescent dyes, such as those described above. The most preferred fluorescent dyes are those selected from the group consisting of aniline and pyridine derivatives of the fluorescent moieties represented by the above general formulas. Specific examples which are preferred for use in the instant invention include coumarin and especially its aniline containing derivatives. These materials are fluorescent at very low concentration levels. Furthermore, they are soluble in aqueous acid solutions without loss of stability over extended time periods. It has been found that these materials adsorb strongly on the porous gel-like aluminosilicate. Furthermore the aniline derivatives deprotonate at well below pH 10 and therefore are not soluble in basic drilling muds.

It is necessary to provide the above surface-active fluorescent dyes in said solution at a level of at least about 0.1 ppm. Preferably, it is found that at least 10 ppm more preferably at least 100 ppm are sufficient to render the residue of extraction easily detectable by ultraviolet radiation. The upper limit for such surface active fluorescent dyes will be dictated by solubility limits and economy. CL 3. The Process The aqueous extraction solution described above containing at least about 10 ppm of DMC is pumped down an injection well to contact an underground copper oxide ore. The ore body may be porous, or if not sufficiently porous, rendered porous by procedures known in the art such as fracturing, etc. The solution after contacting with said copper ore is removed from a production well. It is known in the art that more than one production well and/or injection wells may be suitably used to insure production of all of the copper contained in the ore body. Various configurations of said injection wells and/or production wells are also taught in the aforementioned 'in situ' solution mining patents. The solution that is recovered from the production well will be depleted in the fluorescent dye which indicates that copper has been extracted into the solution, since the dye is adsorbed on the residue resulting from the extraction of copper from the ore.

The examples given below are given to illustrate the instant invention, however, there is no intention to limit the instant invention except by the appended claims.

EXAMPLE 1

Extraction of Copper from Chrysocolla

DMC was dissolved at 0.10% in 0.1 N $H_2SO_4$ to yield a clear pale yellow homogenous solution having a blue-white fluorescence under a long wavelength mineralight. Addition of dilute sodium hydroxide caused the solution to become cloudy. The dispersed phase was intensely fluorescent while the water phase was not thus demonstrating that this dye had the desired solubility properties, i.e. it would not solubilize in basic drilling mud.

Solutions were prepared at 300 ppm, 100 ppm, and 10 ppm DMC in 0.1 N $H_2SO_4$. A small piece (approx. 10–20 g) of a chrysocolla containing ore was placed in 50 ml of each solution. After a few days at ambient temperature, the pieces were removed and rinsed with deionized water. These pieces were then examined under a long-wavelight mineralight.

Fluorescent veins in the ore were visible where chrysocolla had been extracted. These ranged from blue-green to yellow-green and were visible along veins. The fluorescence was not removed by washing with water or aqueous basic solution.

The ore samples leached at 300 ppm and 100 ppm DMC exhibited about the same intensity in the fluorescent zones. The sample leached with 10 ppm DMC showed fluorescent zones that were somewhat weaker and less continuous than the 100 ppm sample. This suggests that the minimum effective contentration for DMC is about 10 ppm, although other more strongly fluorescent materials are effective at lower levels.

Analysis of the acid solution after the extraction confirms that copper was leached. These solutions contained 1 to 1.5 grams/liter of copper. It was also determined that the fluorescent zones in the ore were not removed by rinsing in dilute aqueous sodium hydroxide. These experiments confirm the applicability of the DMC dye to in situ fluid flow determination. In these experiments, the acid to DMC ratio was very large, however similar behavior will hold over a wide range of acid concentration.

EXAMPLE 2

Detection of DMC and its Stability

The detection of DMC in extraction solutions was accomplished by ultraviolet spectroscopy. DMC was a distinctive spectrum. The sulfate salt of DMC shows a prominent band at $_{max}=382$ nm. This band was sufficiently intense to detect DMC at concentration ranges suitable for use in the field. While the $_{max}$ of this absorption band was not sensitive to the presence of copper iron ($Cu^{+2}$) over the range of about 1 to 5 grams per liter, it was very much pH dependent. At pH=1, the band was nearly undectable, but above pH=3.0, the extinction coefficient was large enough to easily determine solutions in the 10 ppm range. Therefore spent extraction solution was pH adjusted prior to analysis with a spectro-photometer (such as a Bausch & Lamb Spectronic 20).

In order to determine the stability of DMC, one of the copper bearing solutions (1.5 g/l Cu; 10 ppm DMC) from the extraction experiments was held at ambient temperatures for 63 days at a pH of 1. After that time its spectrum was taken at pH 1.2 and at pH 4.4. The pH dependent band at 382 nm was clearly evident, indicating that the DMC was present at about the original concentration. This indicates that the dye was stable to the extraction medium for an extended period of time.

EXAMPLE 3

Consumption of Dye

The consumption of dye can be inferred from the experiments conducted with the assumption that the major cause of removal of the dye from solution is sorption into the silica-gel like framework which remains after the copper ion was leached from the chrysocolla. This assumption is consistent with the observation of fluorescent zones after extraction of the copper bearing veins in the ore sample. The absence of fluorescent areas other than leached residues was also consistent with this assumption.

The decrease in dye concentration during extraction is therefore proportional to the increase in copper concentration in the extraction solution. The ratio of the concentration changes is thus an estimate of the dye consumption to be expected.

Table I presents dye consumption data based on the above rationale for two experiments. These experiments show that dye consumption will be in the range of 1-3 lbs. per 1000 lbs. of copper extracted. These experiments also show that the consumption of the dye will be lower at the lower tracer concentration. Depending on the period of the extraction and the expected copper loading in the production solution, the minimum amount of DMC required can be calculated from Table I.

TABLE I

DYE CONSUMPTION IN EXTRACTION EXPERIMENTS

| Expt. No. (Dye) | Decrease in Dye Conc. mg/l | Increase in $Cu^{+2}$ Conc. g/l | mg Dye Consumed g $Cu^{+2}$ Leached |
|---|---|---|---|
| 44-A (10 ppm) | 1.0 | 1.0 | 1.0 |
| 14-D (100 ppm) | 4.3 | 1.4 | 3.1 |

What is claimed is:

1. A method of tracing the flow of a solution for extracting values from an ore, wherein such extraction leaves behind a residue which comprises:
   (a) providing a surface-active dye which may adsorb on the surface of the residue to yield a product which can be detected by eye or radiation outside the visible range of light, and
   (b) detecting said product.

2. The method of claim 1 wherein said values comprise copper.

3. The method of claim 2 wherein said solution is an aqueous acid solution including $H_2SO_4$.

4. The method of claim 3 wherein said ore is chrysocolla.

5. The method of claim 4 wherein said material is a fluorescent surface active dye.

6. The method of claim 5 wherein said dye is selected from the group consisting of pyridine and aniline derivatives.

7. The method of claim 6 wherein said dye is 7-diethylamino-4-methyl coumarin.

8. The method of claim 7 wherein said product comprises 7-diethylamino-4-methyl coumarin adsorbed on a porous gel-like alumino-silicate.

9. The method of claim 8 wherein said product is detected by irradiating a sample containing said product with ultra violet radiation at a wavelength of about 382 nm.

10. The method of claim 9 wherein said solution contains at least about 10 ppm of 7-diethylamino-4-methyl coumarin.

11. A method of tracing the underground flow of a solution for extracting copper values from an oxide ore wherein such extraction leaves behind an extracted ore which comprises,
   (a) providing a material in said solution which will interact with said extracted ore to form a detectable product,
   (b) flowing said solution underground, in contact with said ore to extract said copper values and form said detectable product,
   (c) recovering said solution, including said extracted copper values, from said extracted ore,
   (d) sampling said extracted ore, and
   (e) analyzing said sample of extracted ore for said detectable product.

12. The method of claim 11 wherein said material is a surface-active dye.

13. The method of claim 12 wherein said dye is fluorescent.

14. The method of claim 13 wherein said surface-active dye is an amine.

15. The method of claim 14 wherein said material is an amine.

16. The method of claim 15 wherein said amine is selected from the group consisting of pyridine and aniline derivatives.

17. The method of claim 16 wherein said amine is a coumarin derivative.

18. The method of claim 17 wherein coumarin derivative is 7-diethylamino-4-methyl coumarin.

19. The method of claim 11 wherein said solution is an aqueous acid solution.

20. The method of claim 19 wherein said solution comprises $H_2SO_4$.

21. The method of claim 20 wherein said material comprises an amine selected from the group consisting of pyridine and aniline derivatives.

22. The method of claim 21 wherein said material is 7-diethylamino-4-methyl coumarin.

23. The method of claim 22 wherein said oxide ore is chrysocolla.

24. The method of claim 23 wherein said extracted ore is analyzed for said detectable product by fluorescing said sample with ultraviolet radiation.

25. The method of claim 23 wherein said sampling comprises drilling into said extracted ore to obtain a core thereof.

26. The method of claim 25 wherein said sample is irradiated at a wavelength of about 382 nm.

27. A method for tracing flow of an aqueous acid solution for extracting copper from an underground chrysocolla ore which comprises
   (a) providing a coumarin derivative in said solution,
   (b) flowing said coumarin derivative containing solution underground to contact said chrysocolla ore,
   (c) extracting said copper into said solution from said chrysocolla ore and thereby forming a porous gel-like alumino-silicate,
   (d) absorbing said coumarin derivative on said porous gel-like alumino-silicate to form a product which is detectable by ultraviolet irradiation,
   (e) recovering a solution including said extracted copper from said product,
   (f) drilling into said porous gel-like alumino-silicate to obtain a sample of said product, and
   (g) irradiating said sample at an ultraviolet wavelength of from about 300 to 400 nm.

* * * * *